(12) United States Patent
Kawakami et al.

(10) Patent No.: US 9,434,992 B2
(45) Date of Patent: Sep. 6, 2016

(54) DIAGNOSIS MARKER, DIAGNOSIS METHOD AND THERAPEUTIC AGENT FOR AMYOTROPHIC LATERAL SCLEROSIS, AND ANIMAL MODEL AND CELL MODEL DEVELOPING AMYOTROPHIC LATERAL SCLEROSIS

(71) Applicant: HIROSHIMA UNIVERSITY, Hiroshima (JP)

(72) Inventors: Hideshi Kawakami, Hiroshima (JP); Hirofumi Maruyama, Hiroshima (JP); Hiroyuki Morino, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 14/195,480

(22) Filed: Mar. 3, 2014

(65) Prior Publication Data
US 2014/0186836 A1 Jul. 3, 2014

Related U.S. Application Data (62) Division of application No. 13/392,497, filed as application No. PCT/JP2010/064313 on Aug. 24, 2010, now abandoned.

(30) Foreign Application Priority Data

Aug. 25, 2009 (JP) ................. 2009-194864
Mar. 15, 2010 (JP) ................. 2010-058294

(51) Int. Cl.
*C12Q 1/68* (2006.01)
*C07H 21/04* (2006.01)
*A61K 31/00* (2006.01)
*C07K 14/47* (2006.01)

(52) U.S. Cl.
CPC ............ *C12Q 1/6883* (2013.01); *A61K 31/00* (2013.01); *C07K 14/47* (2013.01); *A01K 2267/0318* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

2004/0191798 A1* 9/2004 Sarfarazi ................. C07K 14/47
435/6.14

OTHER PUBLICATIONS

Funayama et al. Variants in Optineurin Gene and Their Association With Tumor Necrosis Factor-alpha Polymorphisms in Japanese Patients With Glaucoma. Investigative Ophthalmology & Visival Sciences, 2004. 45(12):4359-4367.*

Rezaie et al. (2005, Genomics 85: 131-138).*
Corcia, P. et al., "Absence of the OPTN mutation in a patient with ALS and familial primary open angle glaucoma", Journal of the Neurological Sciences, vol. 309, XP002694642, Oct. 2011, pp. 16-17.
Drachman, D.B. et al., "Cyclooxygenase 2 inhibition protects motor neurons and prolongs survival in a transgenic mouse model of ALS", Ann. Neurol., vol. 52, No. 6, Dec. 2002, pp. 771-778.
Funakoshi-Tago, M. et al., "Celecoxib potently inhibits TNFα-induced nuclear translocation and activation of NF-κB", Biochem. Pharmacol., vol. 76, No. 5, Sep. 1, 2008, pp. 662-671.
Greenway, M.J. et al., "ANG mutations segregate with familial and 'sporadic' amyotrophic lateral sclerosis", Nat. Genet., vol. 38, No. 4, Apr. 2006, pp. 411-413.
Keifer, J.A. et al., "Inhibition of NF-κB activity by thalidomide through suppression of IκB kinase activity", J. Biol. Chem., vol. 276, No. 25, Jun. 22, 2001, pp. 22382-22387.
Kiaei, M. et al., "Thalidomide and lenalidomide extend survival in a transgenic mouse model of amyotrophic lateral sclerosis", J. Neurosci., vol. 26, No. 9, Mar. 1, 2006, pp. 2467-2473.
Kwiatkowski, Jr., T.J. et al., "Mutations in the FUS/TLS gene on chromosome 16 cause familial amyotrophic lateral sclerosis", Science, vol. 323, No. 5918, Feb. 27, 2009, pp. 1205-1208.
Lagier-Tourenne, C. et al., "Rethinking ALS: The FUS about TDP-43", Cell136, Mar. 20, 2009, pp. 1001-1004.
Maruyama, H. et al., "Mutations of optineurin in amyotrophic lateral sclerosis", Nature, vol. 465, No. 7295, May 13, 2010, pp. 223-226.
Rezaie, T. et al., "Adult-onset primary open-angle glaucoma caused by mutations in optineurin", Science, vol. 295, No. 5557, Feb. 8, 2002, pp. 1077-1079.
Rosen, D.R. et al., "Mutations in Cu/Zn superoxide dismutase gene are associated with familial amyotrophic lateral sclerosis", Nature, vol. 362, No. 6415, Mar. 4, 1993, pp. 59-62.
Shisodia, S. et al., "Cyclooxygenase (COX)-2 inhibitor celecoxib abrogates TNF-induced NF-κB activation through inhibition of activation of IκBα kinase and Akt in human non-small cell lung carcinoma: correlation with suppression of COX-2 synthesis", J. Immunol., vol. 173, No. 3, Aug. 1, 2004, pp. 2011-2022.
Sreedharan, J. et al., "TDP-43 mutations in familial and sporadic amyotrophic lateral sclerosis", Science, vol. 319, No. 5870, Mar. 21, 2008, pp. 1668-1672.
Takahashi, Y. et al., "Development of a high-throughput microarray-based system for neurological disorders and its application to molecular genetics of amyotrophic lateral sclerosis", Archives of Neurology; vol. 65, No. 10, XP002694641, Oct. 2008, pp. 1326-1332.
Vance, C. et al., "Mutations in FUS, an RNA processing protein, cause familial amyotrophic lateal sclerosis type 6", Science, vol. 323, No. 5918, Feb. 27, 2009, pp. 1208-1211.

* cited by examiner

*Primary Examiner* — Christopher M Babic
*Assistant Examiner* — Kimberly A Aron
(74) *Attorney, Agent, or Firm* — Perkins Coie LLP; Viola T. King (57) ABSTRACT

Provided are a diagnosis marker, a diagnosis method, and a therapeutic agent suitable for diagnosing and treating amyotrophic lateral sclerosis (ALS). Also provided are an animal model and a cell model suitable for developing a therapeutic agent and a treatment method for ALS. The diagnosis method for ALS includes: an isolation step in which a nucleic acid is isolated from a specimen taken from a subject; a detection step in which bases expressed in a human chromosome 10 optineurin (OPTN) gene region are detected from the isolated nucleic acid; and a determination step in which it is determined whether or not the detected bases are mutated.

5 Claims, 11 Drawing Sheets

DIAGNOSIS MARKER, DIAGNOSIS METHOD AND THERAPEUTIC AGENT FOR AMYOTROPHIC LATERAL SCLEROSIS, AND ANIMAL MODEL AND CELL MODEL DEVELOPING AMYOTROPHIC LATERAL SCLEROSIS

CROSS REFERENCES TO RELATED APPLICATIONS

This application is a divisional of U.S. patent application Ser. No. 13/392,497, filed May 8, 2012, now abandoned, which is the U.S. National Phase application of International Patent Application No. PCT/JP2010/064313, filed Aug. 24, 2010, and claims priority to Japanese Patent Application No. 2009-194864, filed Aug. 25, 2009, and Japanese Patent Application No. 2010-058294, filed Mar. 15, 2010, each of which is incorporated herein by reference in its entirety.

This application contains an ASCII text file of a sequence listing named 10F063-PCT-US-SEQUENCE_LISTING.txt, created on Aug. 23, 2010, the size of which is 3 kilobytes, and which is incorporated herein by reference.

TECHNICAL FIELD

The present invention relates to a diagnosis marker, diagnosis method and therapeutic agent suitable for diagnosing and treating amyotrophic lateral sclerosis. In addition, the present invention relates to an animal model and a cell model suitable for developing a therapeutic agent and a treatment method for amyotrophic lateral sclerosis.

BACKGROUND ART

Amyotrophic lateral sclerosis (hereafter, ALS) is a fatal condition in which motor neurons in the spinal cord, brain stem and cerebral cortex gradually degenerate. An inherited type of ALS and a late-onset sporadic type in which heredity is not recognized are known. Inherited ALS accounts for around 10% of cases, with sporadic ALS accounting for around 90% of cases. In Non-Patent Literature 1, genes thought to be the cause of inherited ALS (e.g., TDP-43, FUS/TLS) are disclosed.

PRIOR ART LITERATURE

Non-Patent Literature

Non-Patent Literature 1: Rethinking ALS: The FUS about TDP-43, Cell 136, Mar. 20, 2009.

DISCLOSURE OF INVENTION

Problems Overcome by the Invention

However, TDP-43 and FUS/TLS are only 20-30% of the cause of inherited ALS. In addition, finding genes thought to be the cause of sporadic ALS is also desired. Consequently, suitable new methods are being sought for genetic diagnoses of ALS. In addition, an animal model and a cell model suitable for efficient development of a therapeutic agent and a treatment method for treating ALS are also being sought.

In consideration of the foregoing, it is an object of the present invention to provide a diagnosis marker, diagnosis method and therapeutic agent suitable for diagnosing and treating amyotrophic lateral sclerosis. In addition, it is an object of the present invention to provide an animal model and a cell model suitable for developing a therapeutic agent and a treatment method for amyotrophic lateral sclerosis.

Problem Resolution Means

In order to resolve the above problems, a diagnosis marker for amyotrophic lateral sclerosis that is a first aspect of the present invention contains a nucleic acid composed of a base sequence having a mutation in human chromosome 10 OPTN (Optineurin) gene regions.

Out of the OPTN gene regions, it is possible for the bases indicated by the 13207995 region and/or the 13214104 region to be mutated bases.

It is also possible for the base in the 13207995 region to have mutated from cytosine to thymine, or the base in the 13214104 region to have mutated from adenine to guanine.

A diagnosis method for amyotrophic lateral sclerosis that is a second aspect of the present invention has:

an isolation step in which a sample is taken from a subject and a nucleic acid is isolated from this sample;

a detection step in which bases expressed in human chromosome 10 OPTN (Optineurin) gene regions are detected from the isolated nucleic acid; and a determination step in which it is determined whether or not the detected bases are mutated.

In the above determination step, it is possible for a determination to be made as to whether the base in the 13207995 region has mutated from cytosine to thymine, or whether the base in the 13214104 region has mutated from adenine to guanine, out of the OPTN gene regions.

A therapeutic agent for amyotrophic lateral sclerosis that is a third aspect of the present invention is such that when bases expressed in a human chromosome 10 OPTN (Optineurin) gene region have mutated, read-through of these bases is induced.

Out of the OPTN gene regions, it is possible for read-through of the base expressed in the 13207995 region to be induced.

A therapeutic agent for amyotrophic lateral sclerosis that is a fourth aspect of the present invention inhibits activation of the NF-κB transcription factor.

A therapeutic agent for amyotrophic lateral sclerosis that is a fifth aspect of the present invention is such that localization of OPTN coded by a human chromosome 10 OPTN (Optineurin) gene in the cell is made suitable, and/or the loss of function achieved by this localization is compensated for.

It is possible to function for the Golgi body in the cell.

An animal model for outbreaks of amyotrophic lateral sclerosis that is a sixth aspect of the present invention is such that a DNA fragment containing mutated bases in the bases indicated in a human chromosome 10 OPTN (Optineurin) gene region, and/or an expression vector, are introduced.

A cell model for outbreaks of amyotrophic lateral sclerosis that is a seventh aspect of the present invention is sampled from the animal model for outbreaks of amyotrophic lateral sclerosis.

Efficacy of the Invention

With the present invention, it is possible to accomplish genetic diagnosis of ALS. In addition, it is possible to treat ALS. Furthermore, it is possible to develop a therapeutic agent and a treatment method for ALS.

BEST MODE FOR CARRYING OUT THE INVENTION (ALS Diagnosis Marker)

A diagnosis marker for ALS according to a first aspect of the present invention will now be explained. This diagnosis marker is used to predict the appearance of ALS and as a marker for diagnosis by detecting and specifying a specific single nucleotide polymorphism.

First, a single nucleotide polymorphism (hereafter SNP) will be explained. An SNP is a genetic mutation present in different locations in every individual, and in which a diversity of mutated single nucleotides can be seen, when base sequences of the human genome are compared.

SNP sites are thought to occur at several million locations in the human genome. These SNP include some which regulate the occurrence of proteins or have an effect on functions, and it is thought that this is involved in individual differences in such things as physical constitution and susceptibility to disease. Accordingly, by obtaining information regarding SNP, it becomes possible to make diagnoses regarding an individual's constitution and hereditary diseases.

Next, an SNP used as a diagnosis marker for ALS will be shown. The base sequence is based on UCSC Genome Bioinformatics (UCSC Genome Browser on Human March 2006 Assembly (hg18)).

Figure 1:
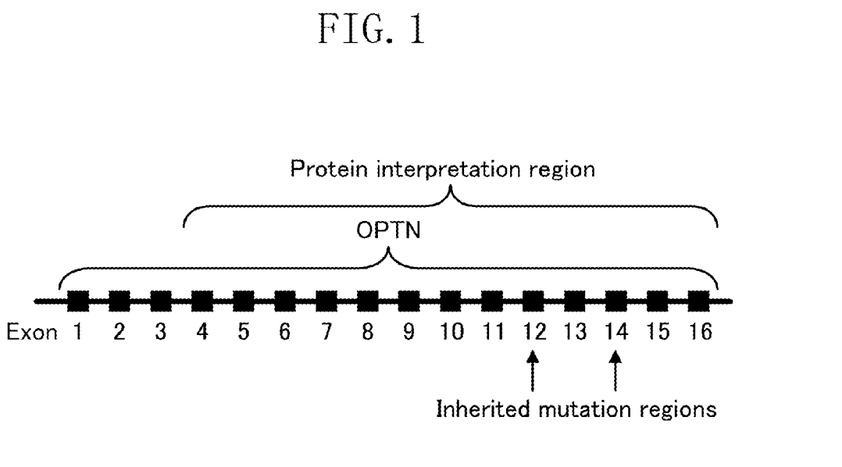
FIG. 1 is a drawing schematically showing the structure of the OPTN gene region.

FIG. 1 schematically shows the structure of the OPTN (Optineurin) gene region. The OPTN gene, which is composed from base sequences in the 13182088-13220282 regions in a human chromosome 10, is composed of from 1 to 16 exons as shown in the drawing. In addition, the protein interpretation region is composed of from 4 to 16 exons. The single nucleotide polymorphism (SNP) exists in the exons between 12 and 14. The SNP used as this diagnosis marker exists in this OPTN.

Sequence number 1 in the sequence table shows the base sequence in the 13207992-13208000 regions in a human chromosome 10 of a healthy person. In addition, sequence number 2 in the sequence table shows the base sequence in the 13207992-13208000 regions in a human chromosome 10 of an ALS patient.

Of these base sequences, when the base in the 13207995 region mutates, there is a possibility that ALS will appear. The base in the 13207995 region mutates from cytosine (C) to thymine (T) in an ALS patient, as shown in sequence numbers 1 and 2.

Next, sequence number 3 in the sequence table shows the base sequence in the 13214100-13214108 regions in a human chromosome 10 of a healthy person. In addition, sequence number 4 in the sequence table shows the base sequence in the 13214100-13214108 regions (the same regions as in sequence number 3) in a human chromosome 10 of an ALS patient.

Of these base sequences, when the base in the 13214104 region mutates, there is a possibility that ALS will appear. The base in the 13214104 region mutates from adenine (A) to guanine (G) in an ALS patient, as shown in sequence numbers 1 and 2.

When the base mutates, functional proteins are not synthesized or abnormal proteins are synthesized, so this is one of the sources of ALS occurring. Accordingly, by detecting and specifying whether or not the bases in the 13207995 region and/or the bases in the 13214104 region have mutated, it is possible to predict the appearance of ALS and diagnose such. That is to say, mutations in these bases are useful as markers for diagnosing ALS.

When one of the bases in the 13207995 region and the 13214104 region has mutated, and in addition when both of the bases have mutated, this becomes a diagnosis marker for ALS.

In addition, this diagnosis marker is an indicator for diagnosing both inherited ALS and late-onset sporadic ALS in which heredity is not recognized.

In addition, this diagnosis marker may be a haplotype having on the same chromosome the base of the 13207995 region or the base of the 13214104 region of a human chromosome 10.

In addition, cDNA, RNA, mRNA, DNA analogs, RNA analogs, amino acids and proteins based on the genes in the 13207995 region and/or the 13214104 region can also be diagnosis markers for ALS.

Mutations in the bases indicated in the 13207995 region and the 13214104 region are one example of OPTN gene mutations. That is to say, all OPTN gene mutations can be diagnosis markers for ALS.

The diagnosis marker explained in the above aspect is not a limitation to the present invention but is disclosed with the intent of illustrating such by example. The technical scope of the present invention is determined by the Scope of Claims, and one skilled in the art could produce various design changes within the technical scope of this invention as noted in the Scope of Claims.

(ALS Diagnosis Method)

Next, an ALS diagnosis method according to a second aspect of the present invention will be described. By taking a sample from a subject, and detecting and specifying the above base mutation (SNP), it is possible to diagnose ALS.

First, a sample is taken from a subject. A commonly known method is used as the method of taking the sample from the subject. For example, it is possible to use a commercially available kit for taking DNA. The sampling method is not limited and may be arbitrary. The sample from the subject may be, for example, a fluid such as blood, cerebrospinal fluid, saliva and/or the like, or tissue such as oral mucus membrane, hair and/or the like, and is arbitrary as long as the sample can be used to detect the above-described SNP. In addition, the volume of the sample is arbitrary as long as the volume is sufficient for the above-described SNP to be detected.

A nucleic acid is isolated from the sample taken from the subject. Here, the nucleic acid is DNA or RNA, and DNA also includes a DNA fragment with the target region amplified by a Polymerase Chain Reaction method in a matrix. The method of isolating the nucleic acid is arbitrary. For example, the DNA can be isolated so as to be suitable for the below-described SNP detection method. In addition, the above-described SNP is in the exons from 12 to 14, as shown in FIG. 1, so it is fine to isolate only the DNA in this range.

Next, the above-described SNP is detected from the DNA and/or the like. The SNP detection method is arbitrary as long as such is a method that can detect and specify the above-described SNP. Specifically, methods that can be cited include a PCR (Polymerase Chain Reaction) method, a PCR-SSP (Sequence Specific Primers) method, a PCR-RFLP (Restriction Fragment Length Polymorphism) method, a PCR-SSCP (Single Strand Conformation Polymorphism) method, a direct sequence method, an ASO (Allele Specific Oligonucleotide) hybridization method, a DGGE (Denaturing Gradient Gel Electrophoresis) method, an RNaseA cutting method, a chemical cutting method, a DOL (Dye-labeled Oligonucleotide Ligation) method, an invader method, a TaqMan (registered trademark)-PCR method, a MALDI-TOF/MS (Matrix-Assisted Laser Desorption Ionization-Time-of-Flight Mass Spectrometry) method, a TDI (Template-directed Dye-terminator Incorporation) method, a molecular beacon method, a dynamic allele-specific hybridization method, or a padlock probe method, and/or the like. In the present embodiment, these SNP detection methods may be used alone, or two or more may be used in combination.

Furthermore, it is determined whether or not the base in the 13207995 region has mutated from cytosine to thymine, and/or whether or not the base in the 13214104 region has mutated from adenine to guanine. When this base has mutated, functional proteins cannot be synthesized or abnormal proteins are produced, so this becomes one source of ALS appearing.

With the above process, it is possible to predict and diagnose the occurrence of ALS.

(ALS Therapeutic Agents)

Next, therapeutic agents for ALS according to the third through fifth aspects of the present invention will be described.

As described above, there is a possibility of ALS occurring when the base in the 13207995 region has mutated from cytosine to thymine. In this case, the base in the 13207995 region has no corresponding amino acid (and tRNA), and becomes a termination codon (nonsense codon) that is used to terminate synthesis of proteins that are the end product. That is to say, through this mutation an immature terminal codon occurs in the gene. Accordingly, gene defect symptoms are exhibited with functional proteins not being synthesized.

In the case of ALS, with the occurrence of an immature termination codon in just one location, fatal symptoms are exhibited just as if the entire gene was defective. Consequently, by selectively skipping over that thymine that is the source of the immature terminal codon occurring, functional protein synthesis becomes possible. That is to say, by administering to an ALS patient a drug that induces read-through of the base in the 13207995 region, it is possible to cure ALS.

Read-through amounts to weakening the bond between the nonsense codon and the termination factor, promotion bonding of the nonsense codon with some tRNA, causing new amino acid growth and promoting synthesis of proteins.

As a therapeutic agent for ALS, for example PTC124 or gentamicin can be cited. However, this is arbitrary as long as such is a substance having read-through activity that can selectively skip over the nonsense codon of the base in the 13207995 region.

In addition, when the base in the 13207995 region has mutated from cytosine to thymine, there is a possibility of ALS appearing. In the 13214104 region, when the base has mutated from adenine to guanine, there is a possibility of ALS appearing. The mutation in the 13207995 region loses the bonding position of RIP1 (Receptor Interacting Protein 1), and the base in the 13214104 region causes a mutation in the ubiquitin bond location and inhibits RIP1 bonding. Mutations in the 13207995 region and the 13214104 region lose the inhibiting action of NF-κB via RIP1.

NF-κB is one transcription factor having a central role in immunoresponse. The inhibiting action of NF-κB is lost by the bonding of OPTN and RIP1 being lost or diminishing. That is to say, through this mutation, NF-κB is activated.

Consequently, by administering to an ALS patient a drug that regulates (inhibits) activation of the NF-κB transcription factor, it is possible to cure ALS.

Here, the NF-κB transcription factor is a transcription factor composed of a hetero- or homo-dimer of five proteins (p50, p52, p65 (RelA), c-Rel, RelB) having a Rel homology domain.

As a therapeutic agent for ALS, for example DHMEQ (Dehydroxymethlyepoxyquinomicin), Bortezomib, and PDTC (Pyrrolidine dithiocarbamate), which is a NF-κB transcription factor inhibitor, can be cited. However, this may be arbitrary as long as such is a substance having a NF-κB transcription factor inhibiting action.

In addition, ALS appears due to a decline in functions occurring accompanying local changes in OPTN in the cells. The mutated OPTN decreases the function a Golgi body achieves by not being local to the Golgi body. Consequently, by making the locality of the OPTN in the cell suitable, and/or compensating for the loss of function achieved by this localization, it is possible to cure ALS.

As the dosage form of the therapeutic agent for ALS, a medicine taken internally, a medicine given by injection, a suppository, an inhaled medicine and/or the like can be cited. This therapeutic agent can be prepared in agent form suitable for oral administration, administration into tissues (subcutaneous administration, intramuscular administration, intravenous administration and/or the like), topical administration (dermal administration and/or the like), transrectal administration and/or the like using commonly known supplements commonly used in the field of pharmaceutical formulation technology, such as excipients, bonders, pulverizers, lubricants, taste- and smell-masking agents, dissolution-aiding agents, suspensions, coating agents and/or the like.

In addition, besides the above supplements, it is also possible to include other medicines and supplements, such as coloring agents, preservatives, fragrances, flavorings, sweeteners and/or the like. This therapeutic agent is naturally administered in a form suitable for these dosing methods. The volume of the therapeutic agent is arbitrary and can be determined taking into consideration such things as the patient's condition, such as age, weight and/or the like, and the dosing route.

(Creation of Animal Model and Cell Model)

Next, a method of creating an animal model and a cell model for developing and evaluating the treatment method for ALS according to the sixth and seventh aspects of the present invention will be explained. A mutation in the 13207995 region is called "mutation 1", and a mutation in the 13214104 region is called "mutation 2."

Of the mutations in the isolated ALS-causing gene OPTN, for mutation 1, which is a recessive mutation, knock-in mice and knock-out mice are produced and evaluation is made using homozygous individuals. On the other hand, for mutation 2, which is a dominant mutation, knock-in mice and knock-out mice are produced and evaluation is made using heterozygous individuals.

As model animals, it is possible to illustrate by example with mice, rats, guinea pigs, hamsters, rabbits, cats, dogs, sheep, swine, goats, cows and monkeys and/or the like. Of these, mice or rats are preferable when taking into consideration their general-purpose nature and convenience as test animals, and mice are particularly preferable.

In addition, there are no particular limitations on the mice, and it is possible to use commonly known mice. However, it is particularly preferable to use BDF1/C57BL/6N type from the perspectives of it being easy to produce transgenic mice, that such are general-purpose and that there is a wealth of information such as genetic background.

(Transgenic Mice)

For mutation 2, which is a dominant mutation, transgenic mice are produced in order to take into consideration the effect the amount of expression has on the seriousness of ALS. Transgenic mice are also produced that express mutation 2 in a promoter base derived from the OPTN gene.

First, the promoter of the gene OPTN is isolated and a construct is produced linking polyA and human cDNA having the human mutation 2 in this promoter. Next, this construct is injected into fertilized mouse eggs to produce transgenic mice. As a nerve-specific expression, a contrast is produced linking polyA and human cDNA having a human mutation 2 in the THY-1 promoter, and transgenic mice are produced.

OPTN mutations of the gene can be considered to all induce nerve cell death by causing NF-κB activity to increase. Consequently, a construct including a mutation that causes NF-κB activity to increase, for example a construct linking Ikkβ constitutive active mutant to the promoter of the OPTN gene, is produced and introduced to the mice, and through this a mouse is produced in which ALS appears.

(Knock-in Mice and Knock-Out Mice)

Because mutation 1 and mutation 2 are at Exon 10 and Exon 12 in the OPTN gene of mice, recombination of human OPTN gene cDNA having mutation 1 and mutation 2 in the mouse exon that is the upstream exon is accomplished. This joint-altered gene is introduced to an ES cell through homologous recombination. This is introduced to the mouse ES cell through electroporation, DNA is extracted from the G418-resistant colony obtained, and homologous recombination clones are selected through PCR and the Southern blot method. In order to avoid the possibility of the neo genes having an effect on expression in a gene X, the neo genes are interposed between loxP genes in advance and after a homology recombination clone is obtained, are removed by Cre recombinase. This ES clone is micro-injected into the mouse fertilized egg blastocyst to obtain a chimera mouse, and a heterozygous mouse is obtained by cross-breeding this with a normal mouse. Mutation 2 is thought to be dominant, so observations are conducted using heterozygous mice. On the other hand, mutation 1 is thought to be recessive, so homozygous mice are produced by cross-breeding heterozygous mice, and observations are then conducted. For recessive mutations, knock-out mice are produced. Mouse OPTN genes in which all or a portion of the Exons were lost are introduced through homologous recombination into mouse ES cells, DNA is extracted from the G418-resistant colony obtained, and a homologous recombinant clone is selected through the PCR and Southern blot method. This ES clone is micro-injected into a mouse fertilized egg blastocyst to obtain a chimera mouse, and heterozygous mice are obtained by cross-breeding this with a normal mouse. Homozygous mice are obtained by cross-breeding heterozygous mice with each other, and observations are then conducted.

As methods for introducing recombinant genes into the model animal, there are no particular limitations and for example it is possible to introduce genes using a micro-injection method, a lipofection method or a method of infecting by combining external genes with a retro virus vector, using expression vectors introducing derivative genes. Besides this, the method is arbitrary as long as this is a commonly known method for introducing these genes into a fertilized egg.

In addition, it is possible to select mice having a mutation in the base sequence of the OPTN gene from a library of mice in which ethylnitrosourea and/or the like, which causes unexpected mutations, is administered to mice to artificially induce mutations. After the mice are selected, it is possible to produce mice in which ALS appears through long-term raising and crossbreeding.

The appearance of ALS in these mice can be confirmed through evaluation of behavior such as walking and physical strength, along with survival rate and pathological evaluations and/or the like. Furthermore, in developing and evaluating therapeutic agents for ALS, the same categories, appearance times and progress of the disease can be evaluated, and evaluation of chemical substances linked to the appearance of ALS and inhibiting the progress of the disease can be evaluated. Or, motor neurons or tissue specimens (for example, spinal cord) can be extracted from the animal model, nerve cell death evaluated by culturing cells and organs, and the efficacy of the drug can thereby be determined (Cell Model)

In addition to culturing of organs and cells obtained from the above-described animal model, it is possible to use fibroblasts from the patient's skin, and cell stock rendered invulnerable by SV40 virus and telomerase, and B cell stock rendered invulnerable by the EB virus from peripheral blood, and/or the like. Using these, in response to stimulation (e.g., TNF-α and in addition to this, a caspase inhibitor or something that produces free radicals and activated oxygen, such as $H_2O_2$) to evoke cell death such as apoptosis and necrosis, a substance that works defensively can be evaluated and searched as an indicator of cell survival rates.

In addition, in response to cells having a gene mutation obtained from the patient's skin and/or the like, iPS cells can be produced through commonly known methods. The iPS cells are caused to divide into motor neurons, and a system that induces motor nerve cell death is produced and substances that prevent this are evaluated and found.

Through the above, it is possible to cause ALS to appear in an animal model and a cell model. In addition, by using an animal model and a cell model in which ALS has appeared, it is possible to develop effective therapeutic agents and treatment methods.

Embodiment

Below, the present invention is explained in greater detail using an embodiment, but the technical scope of the present invention is not limited by this illustration.

(Diagnosis of ALS Patients)

For healthy people, patients with inherited ALS and patients with sporadic ALS, mutations in the base in the 13207995 region and the base in the 13214104 region of the human chromosome 10 were examined First, DNA was sampled using a commercially available kit for extracting DNA from healthy people and ALS patients, and following this the genome was investigated using a GeneChip Human Mapping 500K array set (made by Affymetrix).

Mutations were identified by amplifying all of the exons from Exon 4 to Exon 16 using a prescribed primer and determining base sequence, but below the description is for Exons 12 and 14.

A DNA fragment including the exons of the OPTN gene was amplified by PCR using a primer indicating sequence numbers 5-8 in the sequence table. The base sequence was determined using a direct base sequence determining method on the amplified DNA fragment, and mutations in these bases were identified. After identification, the Exon 12 was cut using restriction enzyme MseI, and the size of the cut DNA fragment was analyzed using 2% agarose gel electrophoresis. Mutations in the bases were determined from differences in the length.

Sequence numbers 5 and 7 indicate a forward primer. Sequence numbers 6 and 8 indicate reverse primers. The primers of sequence numbers 5 and 6 were caused to react with the Exon 12 side, and the primers of sequence numbers 7 and 8 were caused to react with the Exon 14 side, and DNA fragments including the Exon 12 and the Exon 14 of the OPTN gene were amplified.

Figure 2:
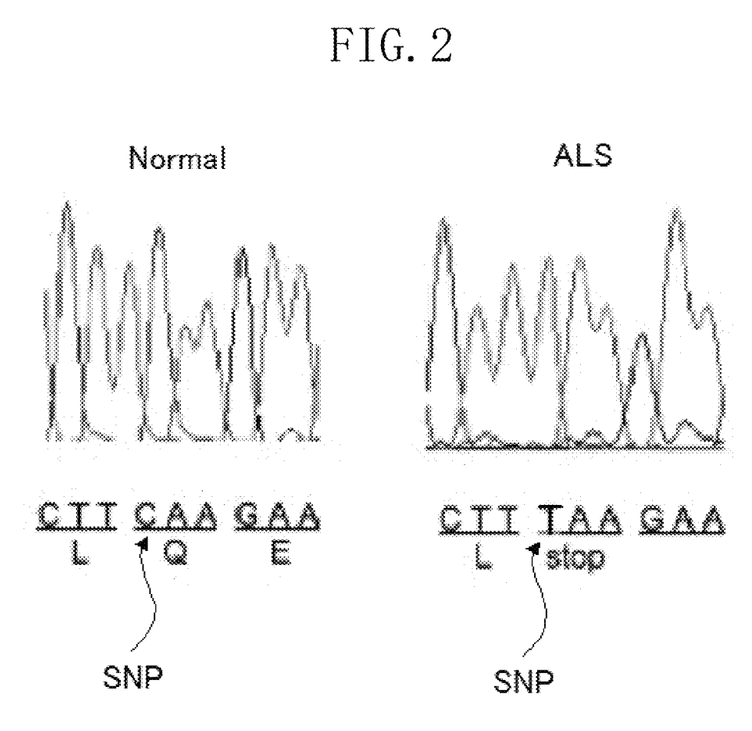
FIG. 2 is a drawing comparing mutations in the base sequence in the 13207992-13208000 regions in a human chromosome 10 of a healthy person and an ALS patient.
Figure 3:
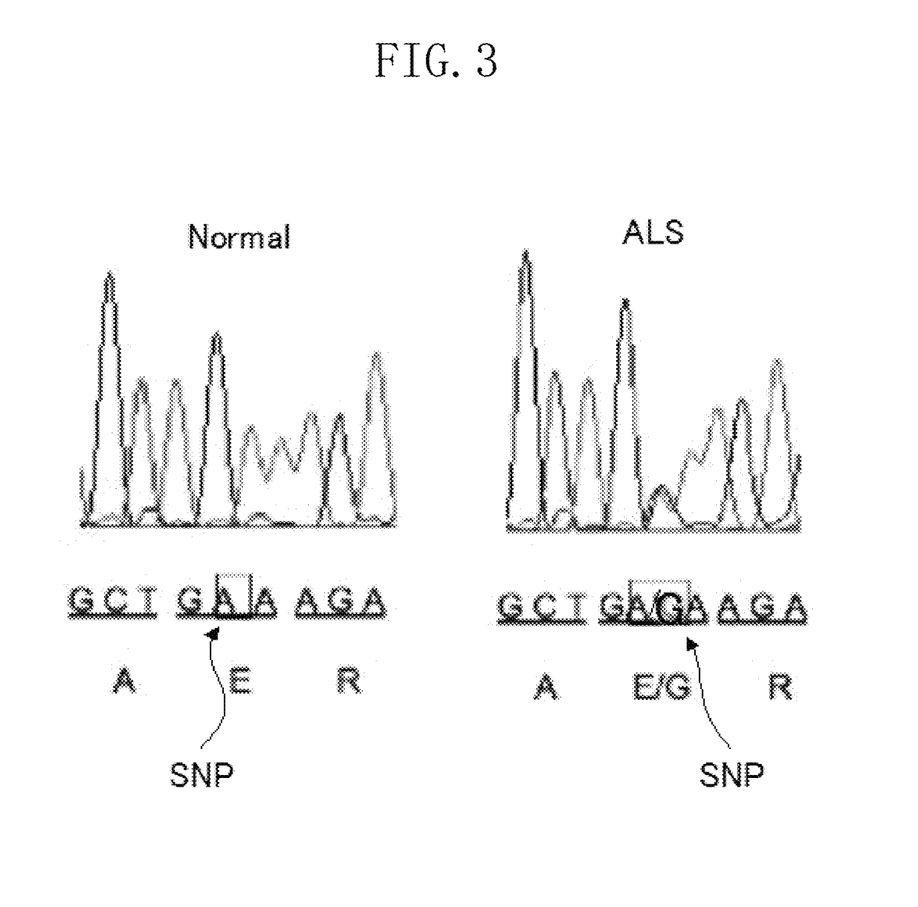
FIG. 3 is a drawing comparing mutations in the base sequence in the 13214100-13214108 regions in a human chromosome 10 of a healthy person and an ALS patient.

FIG. 2 is a drawing comparing mutations in the base sequence in the 13207992 to 13208000 regions of a human chromosome 10 in a healthy person and an ALS patient. FIG. 3 is a drawing comparing mutations in the base sequence in the 13214100 to 13214108 regions of a human chromosome 10 in a healthy person and an ALS patient. The ALS patient shown in FIG. 2 is an ALS patient having a mutation with an autosomal recessive trait. The ALS patient shown in FIG. 3 is an ALS patient having a mutation with an autosomal dominant trait.

As shown in FIG. 2, the base in the 13207995 region of the healthy (normal) person was cytosine (C), and that base in the inherited ALS patient and the sporadic ALS patient had mutated to thymine (T).

In addition, as shown in FIG. 3, the base in the 13214104 region of the healthy (normal) person was adenine (A), and that base in the inherited ALS patient had mutated to guanine (G).

From the above results, it was established that ALS appears when the bases in the 13207995 region and the 13214104 region mutate. In addition, by examining the mutations of these bases, it is possible to diagnose whether the condition is inherited or sporadic ALS.

Figure 4:
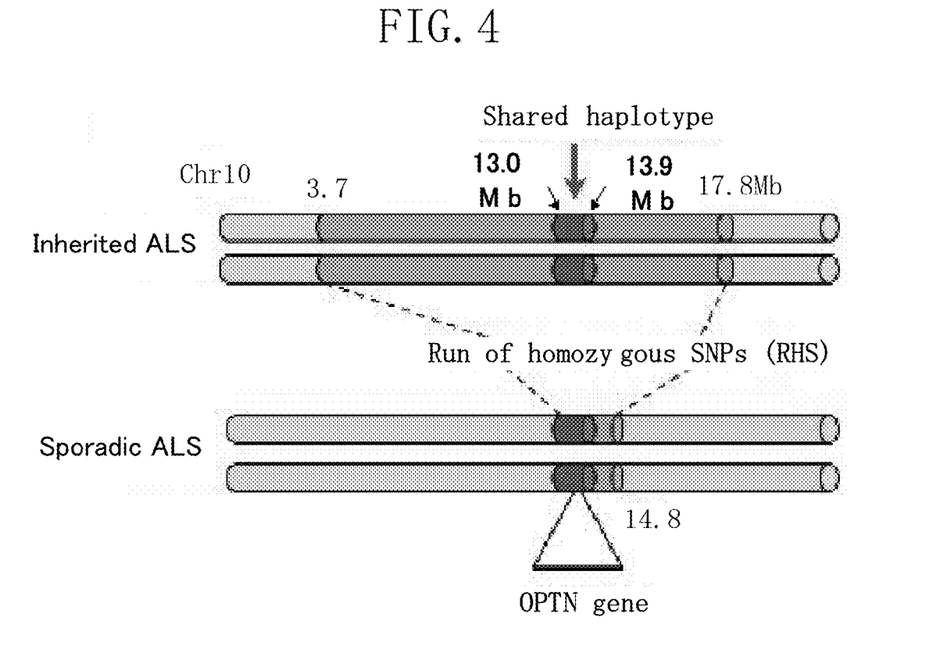
FIG. 4 is a drawing showing a shared haplotype in inherited ALS and sporadic ALS.

FIG. 4 is a drawing showing the haplotype shared in sporadic ALS and inherited ALS. As shown in FIG. 4, a shared haplotype exists in the 13.0 Mb to 13.9 Mb region of a human chromosome 10 in both inherited ALS and sporadic ALS.

In addition, in the ALS patient shown in FIG. 3, a shared haplotype exists in a roughly 2.3 Mb region from region 11460985 to 13703017 of a human chromosome 10.

It is rare for a haplotype to be shared by chance over a 1.0 Mb region or more. Consequently, by examining mutation of the bases in this haplotype, it was possible to diagnose whether the condition was inherited or sporadic ALS.

(OPTN Expression)

Next, for the mutation in the 13207995 region, expression of the OPTN was examined using lysates of transcription lymphoblasts indicating 74 kDa corresponding to OPTN, using a Western blot method. For inherited ALS patients, cell lysates were processed by B lymphocytes rendered invulnerable by an EB virus. In addition, for a healthy person, a normal protocol was used.

Figure 5:
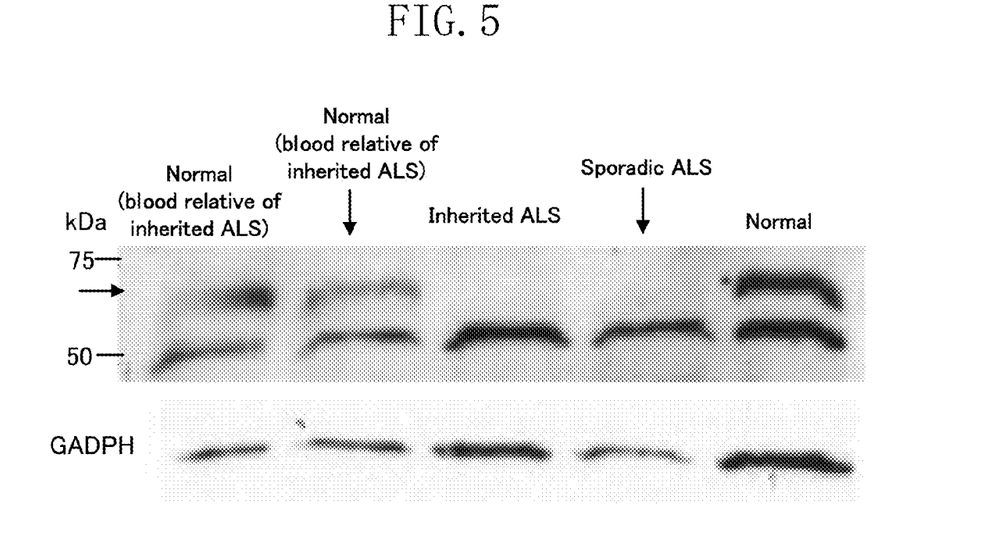
FIG. 5 is a drawing comparing OPTN expression in a healthy person and an ALS patient.

FIG. 5 is a drawing comparing expression of OPTN in a healthy person and an ALS patient. In this drawing, expression for a healthy person (a blood relative of the inherited ALS patient shown third from the left), a healthy person (a blood relative of the inherited ALS patient shown third from the left), an inherited ALS patient, a sporadic ALS patient and a healthy person are shown in order from the left. A polyclonal antibody that recognizes the C terminal portion of the OPTN (made by Cayman Chemical) and the anti-rabbit IgG-HRP antibody (made by R&D Systems) were used. In addition, as a control a polyclonal antibody (made by IMGENEX) for GAPDH (Glyceraldehye-3-phosphate dehydrogenase) was used.

As shown in this drawing, no expression was observed in the 74 kDa region for an inherited ALS patient or a sporadic ALS patient. On the other hand, expression was observed for healthy people. That is to say, it was established that OPTN is not expressed due to mutation of the base in the 13207995 region in ALS patients. Accordingly, it was possible to diagnose ALS using a Western blot method.

Figure 6:
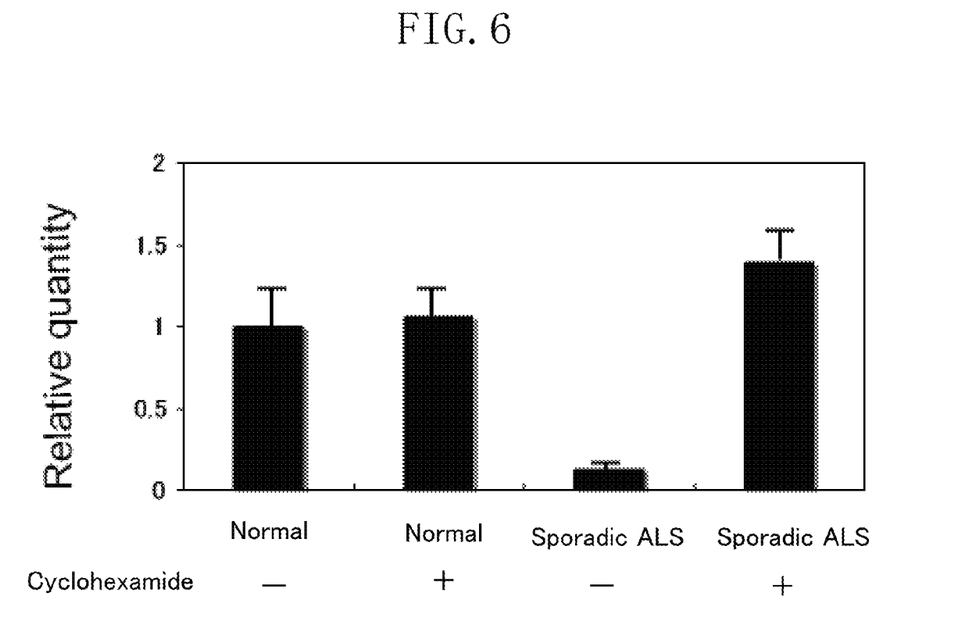
FIG. 6 is a drawing comparing the amount of OPTN expression amplified by RT-PCR.

In addition, FIG. 6 is a drawing comparing the expression quantity of OPTN amplified by RT-PCR (Reverse Transcription-Polymerase Chain Reaction) when cyclohexamide was added and not added in cultured cells of a healthy person and a sporadic ALS patient. In order from the left, the drawing shows the expression quantity of OPTN in a healthy person cultured with no cyclohexamide added, the expression quantity of OPTN in a healthy person cultured with cyclohexamide added, the expression quantity of OPTN in a sporadic ALS patient cultured with no cyclohexamide added, and the expression quantity of OPTN in a sporadic ALS patient cultured with cyclohexamide added.

In order to quantify the OPTN mRNA, RT-PCR was performed using a Thunderbird SYBR qPCR Mix (made by Toyobo Co. Ltd.) and an ABI 7900HT Fast Real Time PCR system (made by Applied Biosystems Inc.). In addition, using primers indicated by sequence numbers 9 and 10 in the sequence table, DNA fragments containing OPTN were amplified by RT-PCR. In addition, prior to extracting RNA, B lymphocytes rendered invulnerable by EB virus were processed for two hours by cyclohexamide (100 mg/ml, made by Sigma).

As shown in the figure, when cyclohexamide is not added, the expression quantity of OPTN in a sporadic ALS patient declined by 13.8% compared to a healthy person. In other words, because a mutation exists in the mRNA of a sporadic ALS patient, translation ends quickly, and through this the expression quantity of OPTN in the sporadic ALS patient declined compared to a healthy person. Accordingly, it was possible to diagnose ALS by comparing the expression quantity of OPTN.

In addition, when a mutation exists in mRNA as in a sporadic ALS patient, it is thought that mRNA is decomposed by the action of nonsense-mediated mRNA decay (NMD) in the lymphocytes, so the expression quantity of OPTN declines. Hence, cyclohexamide, which can return the decline in mRNA accompanying mutations in the amino acid sequence to a normal state, was added and amplification accomplished by RT-PCR. As shown in this figure, in a sporadic ALS patient, there was a large difference in the expression amount of OPTN between when cyclohexamide was added and was not added. This it because by adding cyclohexamide, the action of NMD is inhibited and mRNA decay is blocked, so the OPTN of the sporadic ALS patient could be expressed similar to a healthy person. Accordingly, an NMD inhibitor such as cyclohexamide was shown to be a therapeutic agent for ALS.

(Inclusion Body Immunostaining)

Next, inclusion bodies in the cytoplasm immunolabeled by anti-OPTN antibodies in inherited and sporadic ALS patients were examined FIG. 7 is a drawing showing immunostaining of inclusion bodies.

OPTN-C is a mouse monoclonal antibody, OPTN-I is a rabbit polyclonal antibody, TDP-43 and SOD1 are antibodies made from mouse monoclonal antibodies and rabbit polyclonal antibodies, Ub is ubiquitin, and H&E is hematoxylin and eosin.

Figure 7A:
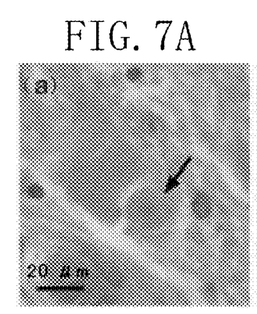
FIGS. 7A to 7M show inclusion body immunostaining.
Figure 7B:
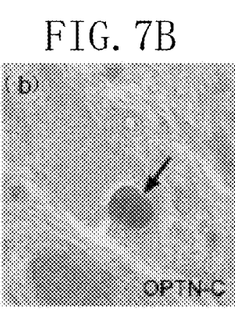
Figure 7C:
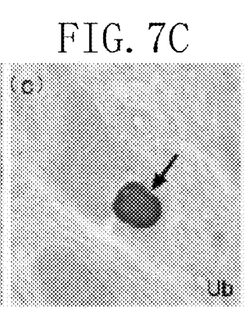
Figure 7D:
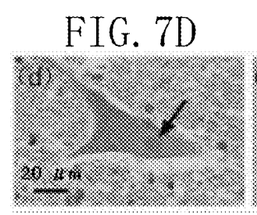
Figure 7E:
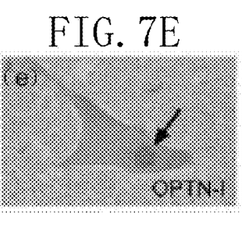
Figure 7F:
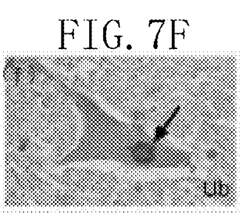
Figure 7G:
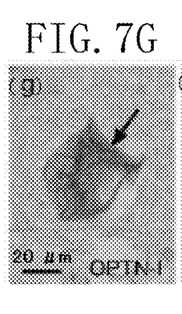
Figure 7H:
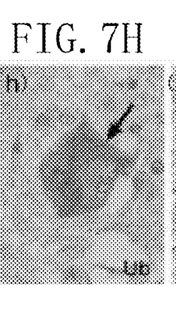
Figure 7I:
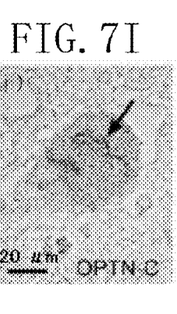
Figure 7J:
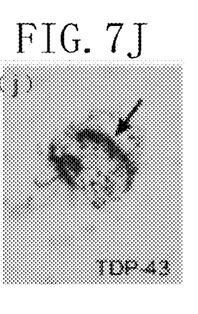
Figure 7K:
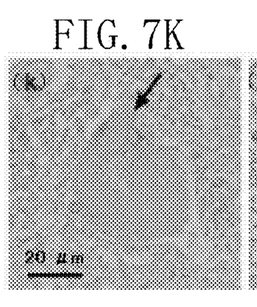
Figure 7L:
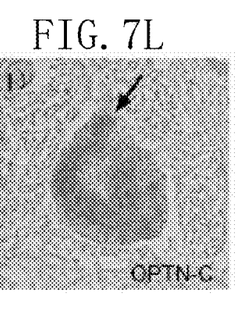
Figure 7M:
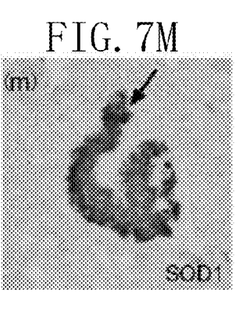
Figure 8A:
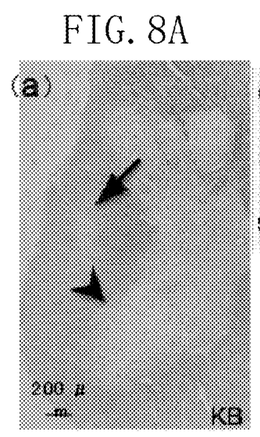
FIGS. 8A to 8H show the spinal cord.
Figure 8B:
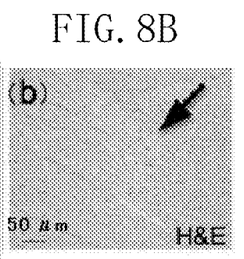
Figure 8C:
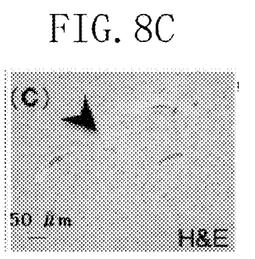
Figure 8D:
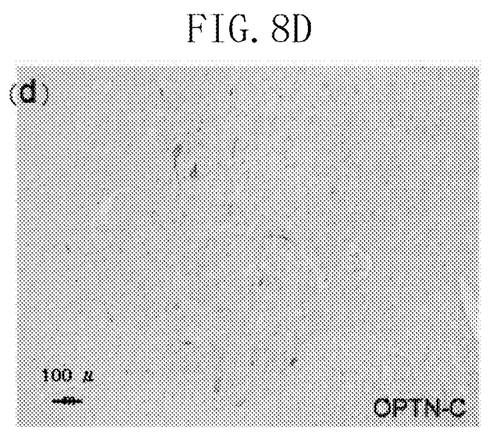
Figure 8E:
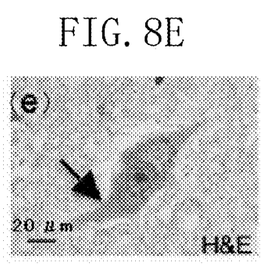
Figure 8F:
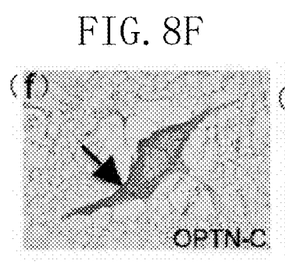
Figure 8G:
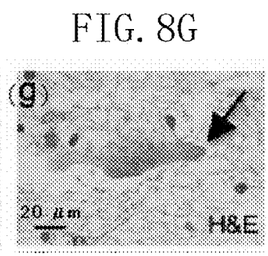
Figure 8H:
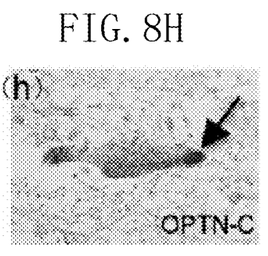
Figure 9A:
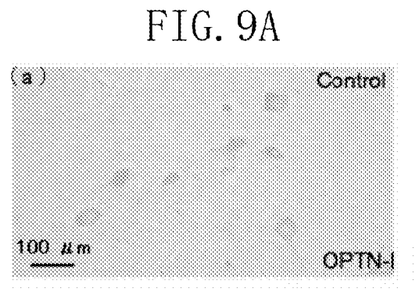
FIGS. 9A to 9D show a comparison of immunostaining of spinal cord anterior horn cells in the pelvic region of a healthy person and an ALS patient.
Figure 9B:
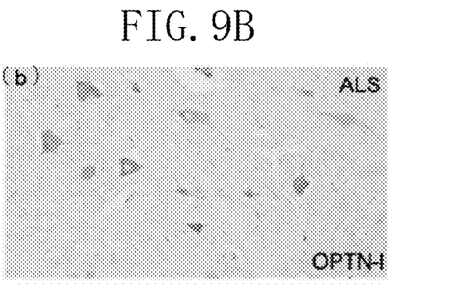
Figure 9C:
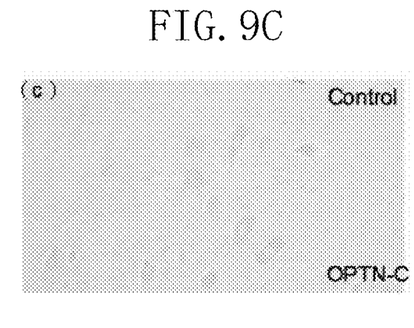
Figure 9D:
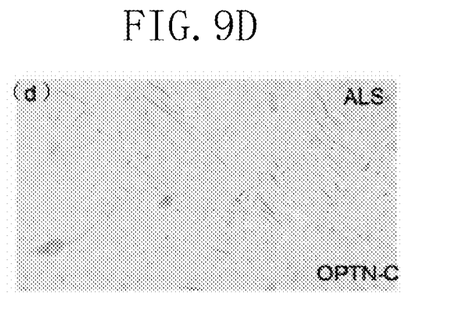

As shown in FIGS. 7A, 7B, 7D and 7E, the eosinophilic hyaline inclusions in a sporadic ALS patient exhibited OPTN immunoreactivity. In addition, as shown in FIGS. 7C and 7F, ubiquitin (Ub) activity was exhibited in the inclusion bodies in the same position as in FIGS. 7A and 7D. In addition, as shown in FIG. 7G, an abnormal fiber structure stained by anti-OPTN antibody was observed. Furthermore, as shown in FIG. 7H, an abnormal fiber structure was similarly stained in the anti-ubiquitin antibody. In addition, as shown in FIGS. 7I and 7J, the immunostaining of a TDP-43 antibody had the abnormal fiber structure stained more clearly compared to OPTN antibody immunostaining. In addition, as shown in FIGS. 7K through 7M, there was OPTN immunoreactive positivity for Lewy-body-like hyaline inclusion with SOD1 immunoreactive positivity.

FIG. 8 shows a spinal cord. As shown in FIGS. 8A and 8C, motor neurons have disappeared in the spinal cord anterior horn in an inherited ALS patient. In addition, as shown in FIGS. 8A and 8B, myelin has disappeared from the corticospinal tract. In addition, as shown in FIG. 8D, with OPTN immunostaining of spinal cord anterior horn cells, the dye strength of motor neuron cytoplasm increased, and intertwined neurites exhibited a reaction to antibodies. In addition, as shown in FIG. 8E, there was an amorphous eosinophilic region in the cytoplasm of the motor neurons. Furthermore, as shown in FIG. 8F, in the same neurons as in FIG. 8E the same location was stained by an anti-OPTN antibody. In addition, as shown in FIG. 8G, something forming a hyaline inclusion body was observed in this kind of eosinophilic region. In addition, as shown in FIG. 8H, the inclusion body of the same neuron as in FIG. 8G was stained by an anti-OPTN antibody. That is to say, with FIGS. 8E and 8G, an eosinophilic inclusion body was recognized in the cytoplasm in the motor neurons. In addition, in FIGS. 8F and 8G, the inclusion body exhibited OPTN immunoreactivity.

In addition, FIG. 9 is a drawing comparing immunostaining of lumbar spinal anterior horn cells of a healthy person and an ALS patient. As shown in FIGS. 9A and 9C, the cytoplasm of the spinal cord anterior horn cells of a healthy person are marked dimly by an anti-OPTN antibody. On the other hand, as shown in FIGS. 9B and 9D, in a sporadic ALS patient staining of OPTN increased in the neurite and the cytoplasm of the spinal cord anterior horn cells.

In a neuro-degenerative disorder such as ALS, the inclusion bodies are a peculiarity of the disease. Consequently, the fact that OPTN was discovered in the inclusion bodies of ALS, and moreover the fact that OPTN was discovered in the cells of sporadic ALS patients without this genetic mutation and moreover in the cells of ALS patients in which a mutation of the SOD1 gene with a different factor gene, indicates the abnormality of OPTN in ALS in general.

Furthermore, an increase in the appearance of OPTN was observed in the axons, neurites and cell bodies of motor neuron.

From the above, NF-κB induces OPTN expression, so by controlling the signal of NF-κB, OPTN expression can be normalized. Accordingly, a therapeutic agent that inhibits the activity of NF-κB transcription factors can be an ALS therapeutic agent.

(Inhibiting NF-κB Activity)

Next, by testing for luciferase, the functions of OPTN in inhibiting the activity of NF-κB were examined. The cDNA of OPTN of an ALS patient was introduced to a pDNR vector (made by Clontech). Using Lipofectamine 2000 (made by Invitrogen Corp.), an NF-κB reporter and an OPTN-infused pDNR vector were introduced into an NSC-34 cell. The luciferase activity was further stimulated by PBS or TNF-α using a dual luciferase reporter assay system (made by Promega Corp.), and measured five minutes later.

Figure 10:
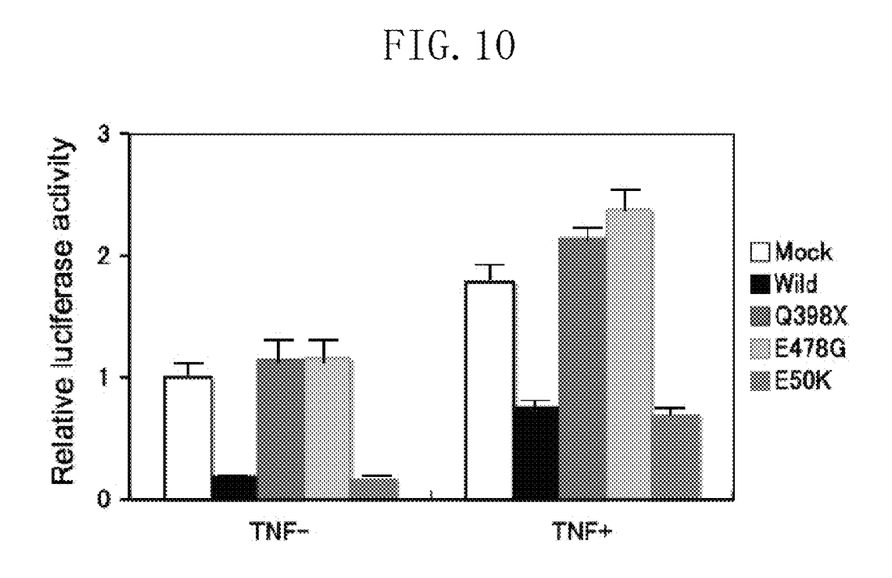
FIG. 10 is a drawing comparing luciferase activity.

The luciferase activity was examined for each mutation of OPTN inhibiting NF-κB activity for both with and without stimulation by TNF-α. FIG. 10 is a drawing comparing luciferase activity.

Q398X is a recessive form of OPTN, E478 is a dominant form of OPTN, and E50K is a mutated strain that evokes glaucoma. In addition, Mock is a pDNR vector. TNF− indicates no TNF-α stimulation, while TNF+ indicates TNF-α stimulation.

As shown in the drawing, the wild type and E50K had an NF-κB activity inhibiting effect. On the other hand, Mock, Q398X and E478 had no NF-κB activity inhibiting effect.

FIG. 11 is a drawing comparing the locality in the cell in a wild type and mutated type of OPTN. For the wild type, Q398X, E478G and E50K, immunofluorescent staining was accomplished by GM130 marking the base of Golgi bodies and FLAG tags.

Figure 11A:
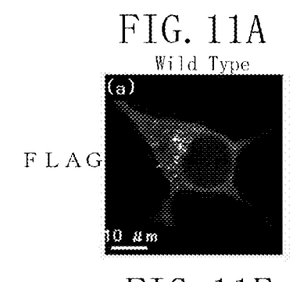
FIGS. 11A to 11L show a comparison of OPTN localization within cells in wild and mutated types.
Figure 11B:
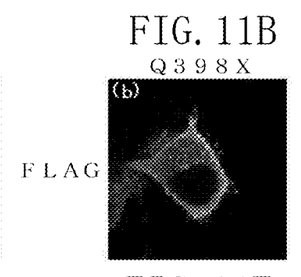
Figure 11C:
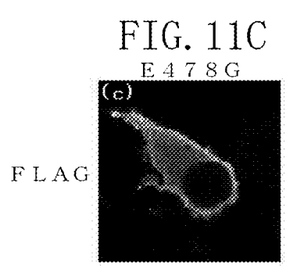
Figure 11D:
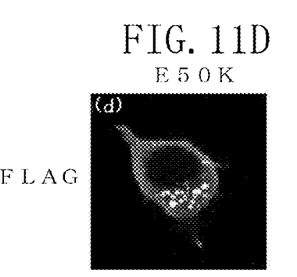
Figure 11E:
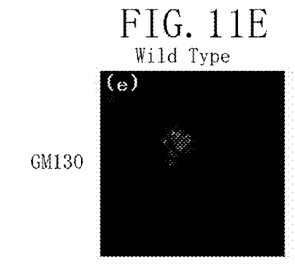
Figure 11F:
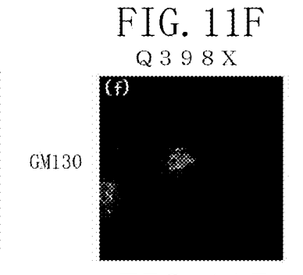
Figure 11G:
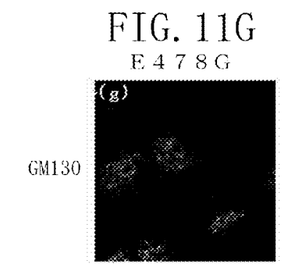
Figure 11H:
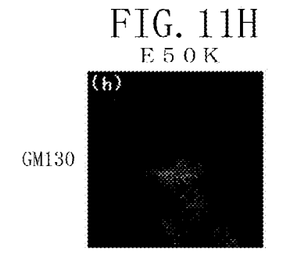
Figure 11I:
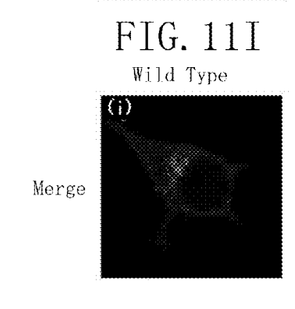
Figure 11J:
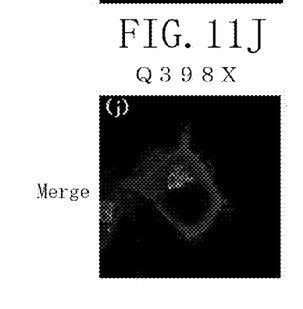
Figure 11K:
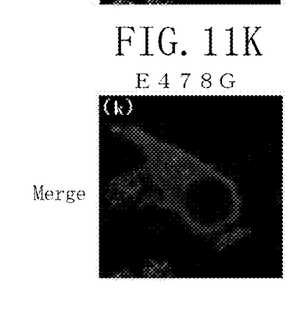
Figure 11L:
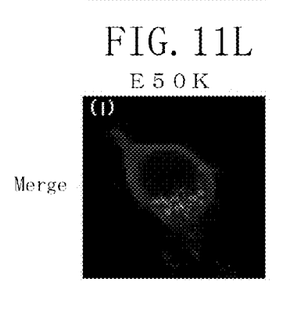

FIGS. 11A through 11D show immunofluorescent staining with FLAG, and FIGS. 11E through 11H show immunofluorescent staining with GM130. FIGS. 11I through 11L (Merge) show the FLAG and GM130 figures superimposed on each other. Specifically, FIG. 11I is FIGS. 11A and 11E, FIG. 11J is FIGS. 11B and 11F, FIG. 11K is FIGS. 11C and 11G and FIG. 11L is FIGS. 11D and 11H, respectively, superimposed on each other.

As shown in FIG. 11I, with wild-type OPTN, many granular OPTN were localized in the Golgi body. On the other hand, as shown in FIGS. 11J and 11K, with Q398X and E478G OPTN, the number of grains declined compared to wild-type, and localization in the Golgi body was hardly observed. As shown in FIG. 11L, with E50K OPTN, grain size is larger than in the wild-type and localization to the Golgi body occurred.

Thus, in the cells of a healthy person, in particular OPTN was localized to the Golgi body. On the other hand, in the cells of an ALS patient, localization of OPTN to the Golgi body declined and accompanying this, loss of functions occurred. Consequently, it was exhibited that by making localization of OPTN reasonable and/or by compensating for function loss achieved by this localization, it is possible to treat ALS symptoms.

From the above, a medicine that makes localization of OPTN in the cells reasonable and compensates for loss of functions achieved by this localization becomes a medicine for treating ALS.

The present application claims the benefits of Japanese Patent Application No. 2009-194864, filed on Aug. 25, 2009, and Japanese Patent Application No. 2010-058294, filed on Mar. 15, 2010, the entire disclosures of which are incorporated by reference herein.

INDUSTRIAL APPLICABILITY

As described above, the diagnosis marker and diagnosis method for ALS according to the present invention can be applied to prediction of ALS appearance and diagnosis of ALS. In addition, the therapeutic agent for ALS according to the present invention can be applied to treating ALS and preventing the appearance of ALS. In addition, the animal model and cell model according to the present invention can be applied when developing therapeutic agents and treatment methods for ALS.

Having described and illustrated the principles of this application by reference to one preferred embodiment, it should be apparent that the preferred embodiment may be modified in arrangement and detail without departing from the principles disclosed herein and that it is intended that the application be construed as including all such modifications and variations insofar as they come within the spirit and scope of the subject matter disclosed herein.

The invention claimed is:

1. A method for diagnosing amyotrophic lateral sclerosis in a human subject, comprising:
   (a) obtaining a sample from a human subject suspected of amyotrophic lateral sclerosis,
   (b) isolating nucleic acids from the sample,
   (c) amplifying DNA fragments from exon 12 of the OPTN (Optineurin) gene by polymerase chain reaction using primers having the sequence of SEQ ID NO: 5 and 6,
   (d) determining whether the base in exon 12 of the OPTN at position 13207995 of chromosome 10 is mutated, and
   (e) diagnosing that the subject has amyotrophic lateral sclerosis if the base is mutated.

2. The method according to claim 1, wherein step (d) determines the mutation of the base from cytosine to thymine.

3. A method for diagnosing amyotrophic lateral sclerosis in a human subject, comprising:
   (a) obtaining a sample from a subject suspected of amyotrophic lateral sclerosis,
   (b) isolating nucleic acids from the sample,
   (c) amplifying DNA fragments from exon 14 of the OPTN (Optineurin) gene by polymerase chain reaction using primers having the sequence of SEQ ID NO: 7 and 8,
   (d) determining whether the base in exon 14 of the OPTN at position 13214104 of chromosome 10 is mutated, and
   (e) diagnosing that the subject has amyotrophic lateral sclerosis if the base is mutated.

4. The method according to claim 3, wherein step (d) determines the mutation of the base from adenine to guanine.

5. The method according to claim 1, further comprising a step after step (c) and before step (d) that cutting the amplified DNA fragments with a restriction enzyme MseI.

* * * * *

SEQUENCE LISTING

```
<160> NUMBER OF SEQ ID NOS: 10

<210> SEQ ID NO 1
<211> LENGTH: 9
<212> TYPE: DNA
<213> ORGANISM: Homo sapiens

<400> SEQUENCE: 1 cttcaagaa                                                              9

<210> SEQ ID NO 2
<211> LENGTH: 9
<212> TYPE: DNA
<213> ORGANISM: Homo sapiens

<400> SEQUENCE: 2 ctttaagaa                                                              9

<210> SEQ ID NO 3
<211> LENGTH: 9
<212> TYPE: DNA
<213> ORGANISM: Homo sapiens

<400> SEQUENCE: 3 gctgaaaga                                                              9

<210> SEQ ID NO 4
<211> LENGTH: 9
<212> TYPE: DNA
<213> ORGANISM: Homo sapiens

<400> SEQUENCE: 4 gctggaaga                                                              9

<210> SEQ ID NO 5
<211> LENGTH: 20
<212> TYPE: DNA
<213> ORGANISM: artificial sequence
<220> FEATURE:
<223> OTHER INFORMATION: A forward primer reacts with exon 12 side.

<400> SEQUENCE: 5
cgtggggtga taaaggtagg                                                 20

<210> SEQ ID NO 6
<211> LENGTH: 22
<212> TYPE: DNA
<213> ORGANISM: artificial sequence
<220> FEATURE:
<223> OTHER INFORMATION: A reverse primer reacts with exon 12 side.

<400> SEQUENCE: 6
```

```
ggaaaacaac ctttgaaacc ag                                              22

<210> SEQ ID NO 7
<211> LENGTH: 22
<212> TYPE: DNA
<213> ORGANISM: artificial sequence
<220> FEATURE:
<223> OTHER INFORMATION: A forward primer reacts with exon 14 side.

<400> SEQUENCE: 7
gggctattga aggatacagc ac                                              22

<210> SEQ ID NO 8
<211> LENGTH: 18
<212> TYPE: DNA
<213> ORGANISM: artificial sequence
<220> FEATURE:
<223> OTHER INFORMATION: A reverse primer reacts with exon 14 side.

<400> SEQUENCE: 8
gcgcgaacac agctattc                                                   18

<210> SEQ ID NO 9
<211> LENGTH: 21
<212> TYPE: DNA
<213> ORGANISM: artificial sequence
<220> FEATURE:
<223> OTHER INFORMATION: A primer is used in RT-PCR.

<400> SEQUENCE: 9
tggaacaggc taaaacagag g                                               21

<210> SEQ ID NO 10
<211> LENGTH: 20
<212> TYPE: DNA
<213> ORGANISM: artificial sequence
<220> FEATURE:
<223> OTHER INFORMATION: A primer is used in RT-PCR.

<400> SEQUENCE: 10
gccctgtcca cttttctga                                                  20
```